United States Patent
Gagnon et al.

(10) Patent No.: US 6,175,116 B1
(45) Date of Patent: Jan. 16, 2001

(54) HYBRID COLLIMATION AND COINCIDENCE IMAGER FOR SIMULTANEOUS POSITRON AND SINGLE PHOTON IMAGING

(75) Inventors: Daniel Gagnon, Twinsburg; Frank P. DiFilippo, Strongsville, both of OH (US)

(73) Assignee: Picker International, Inc., Cleveland, OH (US)

( * ) Notice: Under 35 U.S.C. 154(b), the term of this patent shall be extended for 0 days.

(21) Appl. No.: 09/065,743

(22) Filed: Apr. 24, 1998

Related U.S. Application Data

(63) Continuation-in-part of application No. 60/048,272, filed on Jun. 2, 1997.

(51) Int. Cl.[7] .................................................. G01T 1/164
(52) U.S. Cl. ................................ 250/363.03; 250/363.04; 250/363.02; 250/362; 250/363.1; 378/4
(58) Field of Search .......................... 250/363.04, 363.03, 250/363.02, 363.01, 362, 366, 370.08, 370.09, 370.11, 363.1; 378/4

(56) References Cited

U.S. PATENT DOCUMENTS

| | | | |
|---|---|---|---|
| 5,479,021 | * 12/1995 | Morgan et al. | 250/363.04 |
| 5,481,115 | * 1/1996 | Hsieh et al. | 250/363.04 |
| 5,486,700 | * 1/1996 | Silberklang et al. | 250/363.04 |
| 5,489,782 | * 2/1996 | Wernikoff | 250/363.04 |
| 5,552,605 | * 9/1996 | Arata | 250/363.04 |
| 5,638,817 | * 6/1997 | Morgan et al. | 128/653.1 |
| 5,717,212 | * 2/1998 | Fulton et al. | 250/363.05 |
| 5,760,401 | * 6/1998 | Nelleman et al. | 250/363.03 |
| 5,834,780 | * 11/1998 | Morgan et al. | 250/363.04 |
| 5,838,009 | * 11/1998 | Plummer et al. | 250/363.05 |
| 5,923,038 | * 7/1999 | DiFilippo et al. | 250/363.04 |
| 5,929,446 | * 7/1999 | Plummer et al. | 250/363.05 |
| 5,965,891 | * 10/1999 | Weinberg | 250/363.02 |
| 5,969,358 | * 10/1999 | DiFilippo et al. | 250/363.03 |
| 5,998,792 | * 12/1999 | DiFilippo et al. | 250/363.05 |

* cited by examiner

*Primary Examiner*—Seungsook Ham
*Assistant Examiner*—John Patti
(74) *Attorney, Agent, or Firm*—Timothy B. Gurin; John J. Fry; Eugene E. Clair

(57) ABSTRACT

A gamma camera includes detector heads disposed about an examination region. A high energy collimator collimates the radiation received by each of the detector heads. Either a positron emitting radionuclide or a positron emitting radionuclide and a single photon emitting radionuclide is introduced into an object to be imaged. Radiation which is received by the detectors within a coincidence time interval and radiation which is received by either of the detectors but having an energy characteristic of a positron annihilation are used to generate coincidence data. Radiation which is not indicative of coincidence radiation but which has an energy characteristic of the single photon emitting radionuclide is used to generate single photon data. The data is processed and used to generate one or more images of the object.

15 Claims, 3 Drawing Sheets

HYBRID COLLIMATION AND COINCIDENCE IMAGER FOR SIMULTANEOUS POSITRON AND SINGLE PHOTON IMAGING

This application is a continuation-in-part of U.S. Provisional Application Ser. No. 60/048,272 filed Jun. 2, 1997.

BACKGROUND OF THE INVENTION

The present invention relates to the art of diagnostic imaging. It finds particular application in conjunction with nuclear or gamma cameras and will be described with particular reference thereto. It is to be appreciated, however, that the present invention will also find application in other non-invasive investigation techniques and imaging systems such as single photon planar imaging, whole body nuclear scans, positron emission tomography (PET) and other diagnostic modes.

Positron emission tomography (PET) scanners are known as coincidence imaging devices. In planar coincidence imaging, two radiation detectors oppose each other with a subject disposed between the detectors. Typically, one or more radiopharmaceuticals or radioisotopes capable of generating positron emission radiation are injected into the subject. The radioisotope preferably travels to an organ of interest whose image is to be produced. The detectors scan the subject along a longitudinal axis without rotation, otherwise known as limited angle tomography. Radiation events are detected on each detector and a coincidence circuitry compares and matches the events on each detector. Events on one detector which have a coincident event on the other detector are treated as valid data and may be used in image reconstruction.

Typically, the detector includes a scintillation crystal that is viewed by an array of photo multiplier tubes. The relative outputs of the photo multiplier tubes are processed and corrected, as is conventional in the art, to generate an output signal indicative of (1) a position coordinate on the detector head at which each radiation event is received, and (2) an energy of each event. The energy is used to differentiate between various types of radiation such as multiple emission radiation sources and to eliminate noise, or stray and secondary emission radiation. A two dimensional image representation is defined by the number of coincidence radiation events or counts received at each coordinate. However during a scan, only a fraction of the events detected are coincidence events. As such, scan times are increased in an effort to obtain a sufficient data sampling for image reconstruction which poses additional inconveniences to the subject and an increase in scanning costs.

The present invention provides a new and improved diagnostic imaging system and method which provides simultaneous positron and single photon imaging which overcomes the above-referenced problems and others.

SUMMARY OF THE INVENTION

In accordance with the present invention, a new and improved diagnostic imaging system and method for diagnostic imaging is provided. A nuclear camera system includes a gantry which defines an examination region for receiving a subject. The subject is injected with a substance which emits positron radiation, positron radiation and single photon radiation, positron radiation and radiation suitable to obtain information on attenuation, or any combination thereof. First and second radiation detectors are oppositely disposed on the gantry and have the examination region therebetween. The first and second radiation detectors simultaneously detect radiation from the examination region. A coincidence circuitry connects the first and second radiation detectors and determines the likelihood of that received radiation events come from a positron emitter. Subsystems are connected to the coincidence circuitry which determine the likelihood of a single event having a particular energy band, including an energy window appropriate to define a single gamma of a pair of gamma from a positron emitter, or any other isotopes present in the examination region, including radiation from the positron emitter. An event determiner is connected to the first and second radiation detectors which direct radiation events to a proper reconstruction processor according to characteristics of the radiation events such as timing (or coincidence), energy, location on the detector, or any combination thereof.

In accordance with another aspect of the present invention, a diagnostic imaging method is provided for imaging a subject which includes injecting the subject with first and second isotopes where the first isotope generates positron radiation and the second isotope generates single photon radiation. Selected energy values of radiation are collimated. The positron radiation and the single photon radiation are simultaneously detected and a type of radiation detected is determined. Coincidence data based on the positron radiation detected is generated and single photon data based on the single photon radiation detected is generated. An image representation of the subject is reconstructed from the coincidence data and from the single photon data.

One advantage of the present invention is that positron radiation and single photon radiation arc simultaneously collected by the same radiation detectors.

Another advantage of the present invention is that dual isotope imaging is performed which provides more clinically useful information.

It is a further advantage of the present invention that the image representation of the positron emitter is obtained by selecting events that are in coincidence, events that are in coincidence and with a proper energy, or simply events that have the proper energy, thus increasing the number of events in the final image. Events coming from a different selection path are either immediately combined or separated and analyzed independently.

It is still another advantage of the present invention that an image representation of a single photon emitter (if present in the examination region) is obtained simultaneously with the image representation of the positron emitter.

It is yet another advantage of the present invention that coincidence event image representations that are best when placed in the center of the examination region, can be combined, or analyzed separately with collimated events of the same radiation known to be best at the periphery of the examination region, and to be less affected by the non-uniform nature of attenuation material in the examination region.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
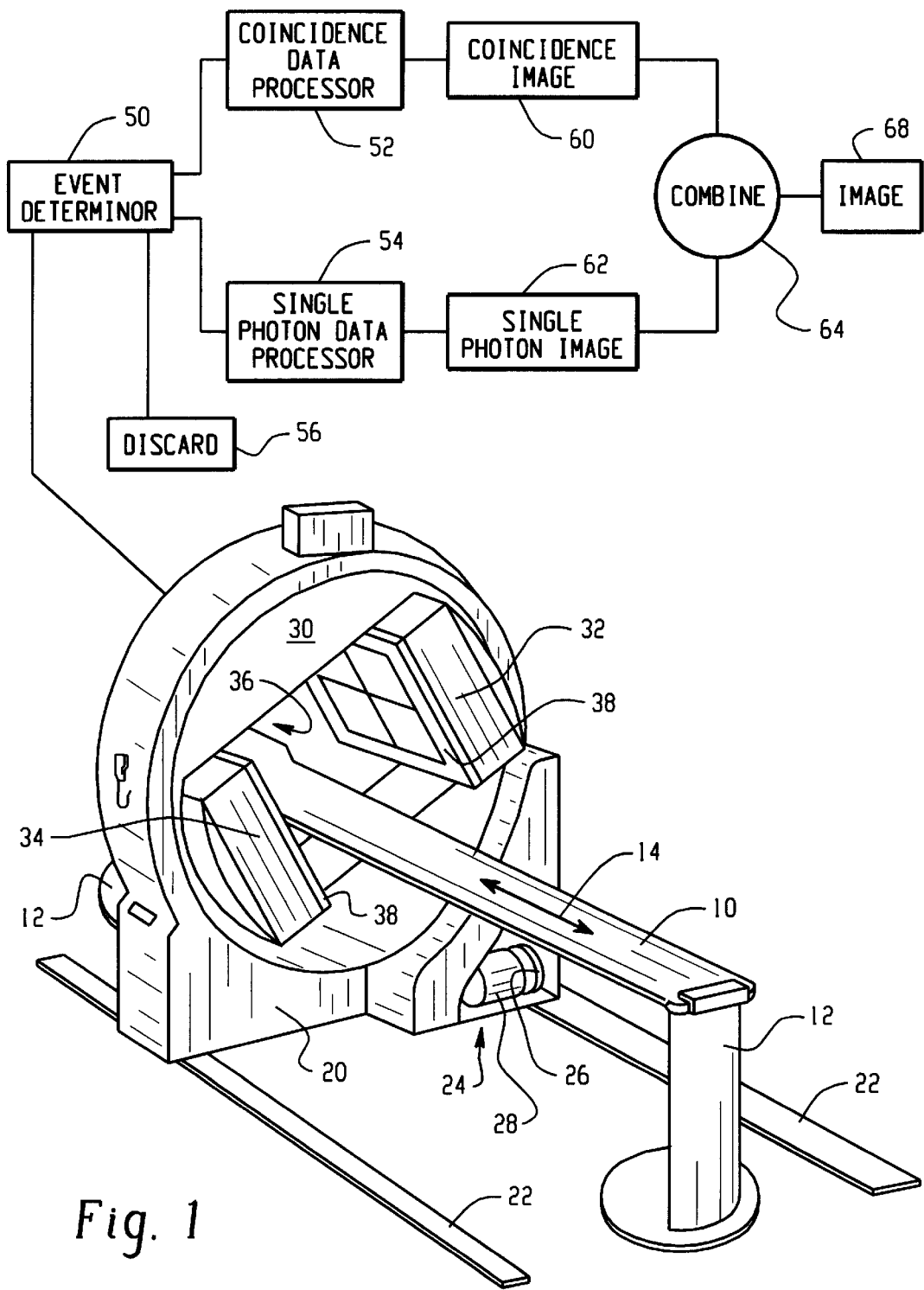
FIG. 1 is a diagrammatic illustration of a diagnostic imaging system in accordance with the present invention.

With reference to FIG. 1, a diagnostic imaging system includes a subject support or table 10 which is mounted to stationary, vertical supports 12 at opposite ends. The subject table is selectively positionable up and down to center a subject 16 in the center of a circle along a longitudinal axis 14. An outer gantry structure 20 is movably mounted on tracks 22 which extend parallel to the longitudinal axis. This enables the outer gantry structure to be moved parallel to the longitudinal axis 14. An outer gantry structure moving assembly 24 is provided for selectively moving the outer gantry structure 20 along the tracks 22 in a path parallel to the longitudinal axis. In the illustrated embodiment, the longitudinal moving assembly includes drive wheels 26 for supporting the outer gantry structure on the tracks. A motive power source, such as a motor 28, selectively drives one of the wheels which frictionally engages the track and drives the outer gantry structure and supported inner gantry structure and detector heads therealong. Alternately, the outer gantry can be stationary and the subject support configured to move the subject along the longitudinal axis.

An inner gantry structure 30 is rotatably mounted on the outer gantry structure 20. A first camera or radiation detector head 32 is mounted to the inner gantry structure. A second radiation detector head 34 is mounted to the inner gantry structure opposite to the first camera head. The first and second detectors 32, 34 are configured to detect positron emission radiation generated by a positron emission source injected into the subject. The inner gantry structure defines a central, subject receiving examination region 36 for receiving the subject table and, particularly along the longitudinal axis. The examination region 36 is enlarged to receive the detector heads in any of a variety of displacements from a central axis and angular orientations.

The detectors each include a scintillation crystal disposed behind a radiation receiving face 38 that is viewed by an array of photo multiplier tubes. The scintillation crystal emits a flash of light in response to incident radiation. The array of photo multiplier tubes convert the light into electrical signals. A resolver circuit resolves the x,y-coordinates of each light flash and the energy of the incident radiation. The relative outputs of the photo multiplier tubes are processed and corrected, as is conventional in the art, to generate an output signal indicative of a position coordinate on the detector head at which each radiation event is received, and an energy of each event.

With further reference to FIG. 1, the overall operation of the present invention may be summarized as follows. A subject to be imaged is injected with one or more isotopes which generate positron radiation, or positron radiation and single photon radiation. In the preferred embodiment, two isotopes are injected which have different energies. For example, a first isotope generates positron radiation in a range of 511 keV and the second isotope is generates single photon radiation in a range of 140 keV. For example, Tc-99 m emits photons having a primary photopeak of approximately 140 keV. During an imaging scan, the radiation detectors 32, 34 both simultaneously detect and collect all types of radiation from the subject and examination region which may include positron coincidence radiation events, single photon radiation events, transmission radiation events, and any combination thereof depending on the radiation sources present. An event determiner 50 evaluates the event data and determines the type of radiation event and/or the type of radiation at each detected event. Based on selected factors of an event such as timing (coincidence between two events), energy, location or any combination of these factors, the radiation data is processed by a coincidence data processor 52, a single event processor 54, or is disregarded 56. The coincidence processor can further direct events to a sub-processor according to location and/or energy of the event. The single photon processor 54 can further direct events to a sub-processor according to location and/or energy of the event. An image representation of each processor and sub-processor can be combined or analyzed separately.

Figure 2:
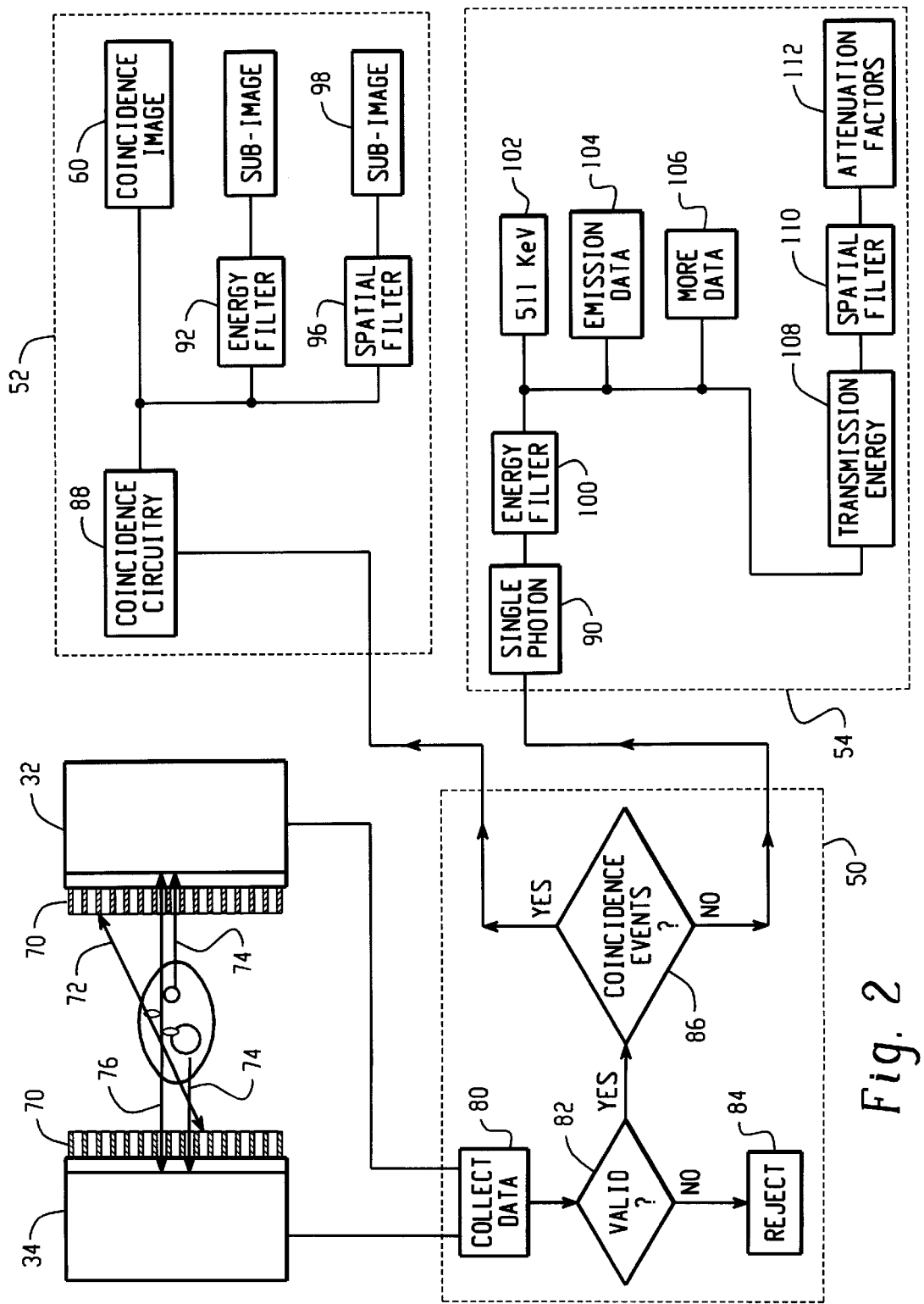
FIG. 2 is an illustration of a preferred embodiment of the present invention.
Figure 3A:
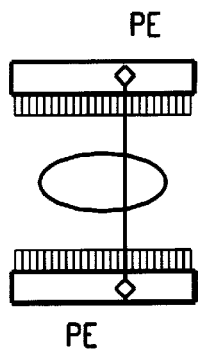
FIGS. 3A–3D illustrates examples of a coincidence events detected.
Figure 3B:
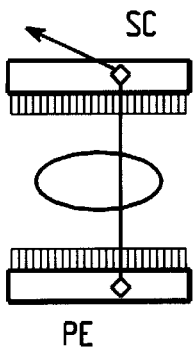
Figure 3C:
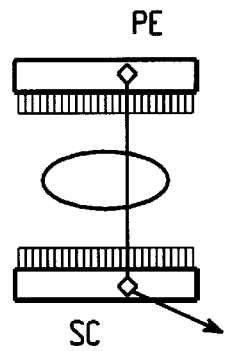
Figure 3D:
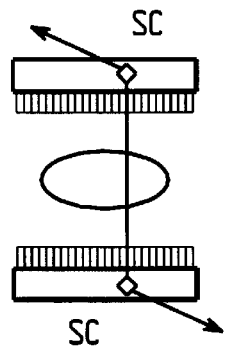

With reference to FIG. 2, a preferred embodiment is shown including a high energy collimator 70 mounted on the radiation receiving face of the detectors 32 and 34. The high energy collimator provides sufficient shielding to filter a large fraction of 511 keV gamma radiation 72 traveling at an angle with respect to an axis of the collimator 70. Thus, single photon radiation 74, coincidence positron radiation 76, single event positron emission radiation, and transmission radiation (if present) which reach the detectors are collimated. The high energy collimator 70 providessufficient spatial filtering in the collimator to produce adequate images from high energy isotopes. Heavy filtering reduces the count rate of received radiation on the detectors allowing for longer integration times to be used to improve performances at low energy.

The high energy collimator 110 geometrically correlates coincidence events from the 511 keV positron emitters. Thus, all coincidence events are accepted as valid events irrespective of their energy. Even the scatter/scatter events which typically comprise a majority of the events occurring a thin scintillation crystal are accepted as valid data which would otherwise be disregarded.

With further reference to FIG. 2, the event determiner 50 collects all data 80 from the radiation events detected by the radiation detectors 32 and 34. Each event is determined 82 whether it is valid based on predefined valid energy windows based on the energy characteristics of the injected isotopes and transmission radiation source (if present). If a detected event does not fall within of the predefined energy windows, the data is disregarded 84 as noise. If the event does fall within the selected energy windows, a determination 86 is made as to whether the event is a coincidence event. Based on this determination, the event data is directed to a coincidence circuitry 88 or a single photon data processor 90.

The coincidence circuitry 88 determines coincidence between events by matching the event with a coincidence event on the other detector and determines a ray path traveled by the event. If a coincidence is found, coincidence data is generated and a coincidence reconstruction processor reconstructs the coincidence data into a coincidence or positron image representation 60. Alternately, the coincidence circuitry 88 directs the event data to an energy filter 92 in a case where the coincidence determination results in a finding that one or both of the coincidence events underwent scattering. In the case of scattering, the event data is filtered and a sub-image 94 is reconstructed. Lastly, if the coincidence circuitry determines that the event resulted from a transmission radiation source, the event data is directed to a spatial filter 96 which filters the transmission event and a sub-image 98 representing a positron transmission source is reconstructed.

If the determination 86 results in the event not falling within the positron energy window, the event data is directed to the single photon processor 90 and an energy filter 100 where the event is processed according to its energy. Radiation data is generated and an image representation is reconstructed in accordance with the type of data which may be 511 keV representing a positron distribution 102, emission data representing a single photon distribution 104, or simple more data 106. If, however, the event data is determined to be transmission energy 108, a spatial filter 110 filters the event data into attenuation factors 112. Once the positron image 60 and the single photon image 62 are reconstructed, the images may be displayed together for analysis or may be selectively combined such as by super imposing one on to the other to generate a resultant image.

Figure 4A:
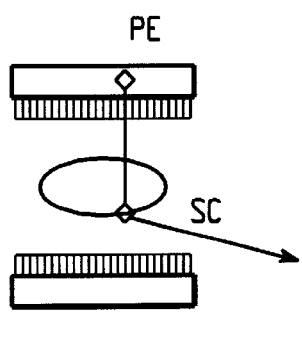
FIG. 4A illustrates an example of a single detected event from a positron emitter.
Figure 4B:
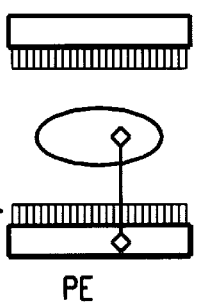
FIG. 4B illustrates an example of a single detected event from a 20 single photon emitter.
Figure 4C:
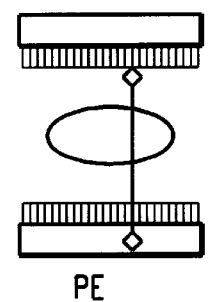
FIG. 4C illustrates an example of a single detected event from transmission radiation.

With reference to FIGS. 3A–3D, examples of possible coincidence events detected by the detectors 32 and 34 are shown, all of which are accepted as valid data. FIGS. 4A–4C illustrate examples of single detected events which are accepted as valid data such as a high energy 511 keV radiation event (FIG. 4A), a low energy 140 keV radiation event (FIG. 4B), and a transmission radiation event (FIG. 4C). A photoelectric effect event is represented by PE and a scatter event is represented by SC. The scatter events are typically disregarded, however with the present system, they are accepted as valid counts available for imaging. This results in an increase in the effective count rate and provides for dual isotope imaging. All detected events having energies which fall within the coincidence window are accepted for positron image reconstruction and all events having energies in anticoincidence and falling within a valid energy window are accepted for single photon reconstruction.

Using the high energy collimator 70, spatial resolution is reduced only if the collimator provides the directional information on the two coincidence 511 keV gammas. An additional spatial constraint can be imposed after the coincidence trigger because the coincident events should be directly opposed to one another on the detectors 32 and 34 plus or minus a few degrees. Adjustments are made to select proper parameters to optimize the count rate and spatial resolution for the positron emitter and to provide sufficient spatial and energy resolution for the low energy single photon isotope.

Preferably, the coincidence circuitry and data processor 52 is used on long integration time events. In this mode, the count rate for the positron emitter is reduced as compared to using a standard bare scintillation crystal. Furthermore, typical coincidence counting using large area detectors is typically eliminated by the dose of the injected isotope, meaning that the injected dosage must be reduced so that the maximum count rate of the system is not exceeded. Thus, a stronger filter (e.g., collimator) can be applied so that the injected dose is not reduced in order to maintain an effective count rate in the image.

The following is an exemplary decision tree process in accordance with a hybrid coincidence/collimation mode.

Figure 5:
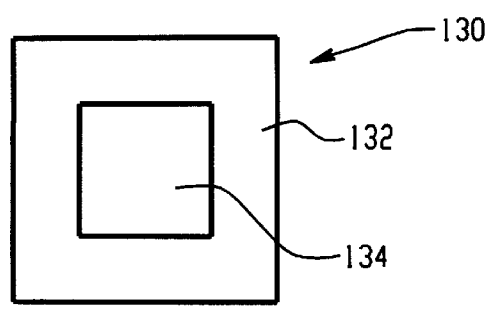
FIG. 5 illustrates an alternative collimator in accordance with the present invention.

Hybrid Coincidence/Collimation Mode
(collecting events of types shown in FIGS. 3A–3D and 4A–4C)
Event detected
   In coincidence with another event on different detector
      Evaluate position of the two events (FIGS. 3A–3D)
      Generate coincidence events data
      Reconstruction
      Distribution of positron emittor using coincidence events
   Single event, no coincidence
      Evaluate energy
      Energy within the 511 keV energy window (FIG. 4A)
         Distribution of positron emittor using single events
      Energy within a single photon energy window (one or several windows) (if defined) (FIG. 4B)
      Distribution of single photon emittor
      Energy within transmission energy window (if defined) (FIG. 4C)
         Distribution(s) of the attenuation coefficient (140 keV and 511 keV)
      Event Rejected With reference to FIG. 5, an alternative collimator 130 is shown which includes a first level of collimation 132 provided to collimate the high energy photons and a finer resolution collimator 134 provided within the large area of the first high-energy collimator. Thus, a one-dimensional axial filter and a high-resolution low energy collimator are combined. However, this configuration does not benefit from the advantageous of the full ultra-high energy collimator 70 and all coincidence events cannot be blindly accepted. The low energy image may be affected from the presence of the high-energy axial filter and from an absence of coincidence filter in the Compton region of the 511 keV isotope.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of examining an object disposed within the examination region of a gamma camera, which camera includes first and second detectors disposed about the examination region, the object including a first radionuclide which generates positron radiation and a second radionuclide which generates single photon radiation, the method comprising:

collimating the single photon radiation and the coincident radiation characteristic of positron annihilations;

utilizing the first and second detectors to detect the collimated radiation;

determining whether the detected radiation is indicative of coincident radiation or single photon radiation;

generating coincidence data based on the detected coincident radiation; and generating single photon data based on the detected single photon radiation.

2. The method of claim 1 wherein the object is a human patient.

3. The method of claim 2 further including utilizing the coincidence data and the single photon data to generate an image of the object.

4. The method of claim 1 further including defining a coincidence time interval and a first energy window which includes a primary photopeak of the second radionuclide and wherein the coincident radiation includes radiation which is detected by both the first and second detectors within the coincidence time interval and which has traveled along a preselected path, and single photon radiation includes radiation which is not the coincident radiation and which has an energy within the first energy window.

5. The method of claim 4 further including defining a second energy window which includes 511 keV and wherein the coincident radiation includes radiation which falls within the second energy window.

6. The method of claim 4 wherein the first energy window includes 140 keV.

7. A method of examining an object disposed within the examination region of a gamma camera, which camera includes first and second detectors disposed about an examination region, the object including a first radionuclide which generates positron radiation, the method comprising:
   collimating coincident radiation characteristic of positron annihilations;
   utilizing the first and second detectors to detect the collimated radiation;
   generating coincidence data based on a first category of detected radiation, the first category of detected radiation including (i) radiation detected by both the first and second detectors within a coincidence time interval and which has traveled along a preselected path; and (ii) radiation detected by either of the first and second detectors and having an energy characteristic of an unscattered positron annihilation.

8. The method of claim 7 further including using the coincidence data to generate an image indicative of positron radiation generated by the first radionuclide.

9. The method of claim 7 wherein each of the detectors include a radiation sensitive face and generate a signal indicative of a position on the face at which the radiation has been detected.

10. The method of claim 7 wherein the preselected path is defined by an acceptance angle of a collimator.

11. The method of claim 7 wherein the object includes a second radionuclide which generates single photon radiation, the method further including:
   defining a energy window which includes a primary photopeak of the second radionuclide;
   collimating the radiation generated by the second radionuclide;
   generating single photon data based on a second category of detected radiation, the second category including radiation which is not within the first category of radiation and which has an energy within the energy window.

12. The method of claim 11 further including utilizing the single photon data to generate an image indicate of the single photon radiation generated by the second radionuclide.

13. An apparatus for examining an object disposed in an examination region, which object includes a first radionuclide which generates positron radiation, the apparatus comprising:
   a first radiation sensitive detector having a radiation sensitive face which faces the examination region;
   a first collimator disposed between the examination region and the radiation sensitive face of the first detector for collimating the coincident radiation characteristic of the positron radiation;
   a second radiation sensitive detector having a radiation sensitive face which faces the examination region;
   a second collimator disposed between the examination region and the radiation sensitive face of the second detector for collimating the coincident radiation characteristic of the positron radiation;
   data processing means operatively connected to the first and second-detectors for generating coincidence data based on a first category of detected radiation, the first category of detected radiation including (i) radiation detected by both the first and second detectors within a coincidence time interval and which has traveled along a preselected path; and (ii) radiation detected by either of the first and second detectors and having an energy characteristic of an unscattered positron annihilation.

14. The apparatus of claim 13 wherein the object includes a second radionuclide which generates single photon radiation, the apparatus including:
   means for collimating the radiation generated by the second radionuclide;
   means for generating single photon data based on a second category of detected radiation, the second category including radiation which is not within the first category of radiation and which has an energy characteristic of a primary photopeak of the second radionuclide.

15. The apparatus of claim 13 wherein the first radiation sensitive detector includes a plurality of photosensitive elements and a layer of scintillating material disposed between the photosensitive elements and the examination region.

* * * * *